(12) United States Patent
Clark et al.

(10) Patent No.: US 6,193,661 B1
(45) Date of Patent: Feb. 27, 2001

(54) SYSTEM AND METHOD FOR PROVIDING DEPTH PERCEPTION USING SINGLE DIMENSION INTERPOLATION

(75) Inventors: David W Clark, Windham; Richard A Hager, Derry, both of NH (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/287,982

(22) Filed: Apr. 7, 1999

(51) Int. Cl.$^7$ ........................................... A61B 8/00
(52) U.S. Cl. ................................. 600/443; 600/447
(58) Field of Search ........................ 600/443, 447; 128/916; 73/625, 626; 382/44–47

(56) References Cited

U.S. PATENT DOCUMENTS

| | | | |
|---|---|---|---|
| 4,448,201 | * 5/1984 | Matsumoto | 600/437 |
| 5,159,931 | 11/1992 | Pini | 128/660.07 |
| 5,388,582 | * 2/1995 | Beni et al. | 600/443 |
| 5,390,674 | * 2/1995 | Robinson et al. | 600/443 |
| 5,396,890 | * 3/1995 | Weng | 600/443 |
| 5,995,108 | * 11/1999 | Isobe et al. | 345/421 |

OTHER PUBLICATIONS

Levoy, "Vol. Rendering Display of Surfaces from Vol. Data," IEEE Computer Graphics & Applications, May 1988, pp. 29–37.

Barillot, "Surface and Vol. Rendering Techniques to Display 3–D Data an Overview of Basic Principles Shows Advances in Display Techniques," IEEE Engineering in Medicine and Biology, Mar. 1993, pp. 111–119.

Pfister, et al., "Sheared Interpolation and Gradient Estimation for Real–Time Vol. Rendering," Eurographics Hardware Workshop, Oslo, Sep. 1994, pp. 1–10.

Lacroute, et al., "Fast Vol. Rendering Using a Shear–Warp Factorization of the Viewing Transformation," Computer Graphics Proceedings, Annual Conference Series, 1994, pp. 451–456.

"Visualization of Surfaces from Volumetric Data," Chapter 3, pp. 35–45, published sometime before Feb. 1998.

* cited by examiner

*Primary Examiner*—Marvin M. Lateef
*Assistant Examiner*—Ali M. Imam

(57) ABSTRACT

Disclosed is a system and method for generating two dimensional renderings on a display device of acoustic volumetric data that provides depth perception to the user. The system includes an acoustic data acquisition circuit, which includes a sonic transducer and other components, that generates and stores an acoustic data set from medium such as a human body, etc. A scan converter generates a perspective volumetric data set of the medium based upon the acoustic data set, and a single dimensional interpolator that generates at least one interpolated data set from the perspective volumetric data set. The perspective volumetric and interpolated data sets are processed by a compositor that generates two dimensional renderings of the perspective volumetric data set and the interpolated data sets. The system includes a display device which displays the two dimensional renderings in a predetermined fashion to provide depth perception to the viewer.

15 Claims, 6 Drawing Sheets

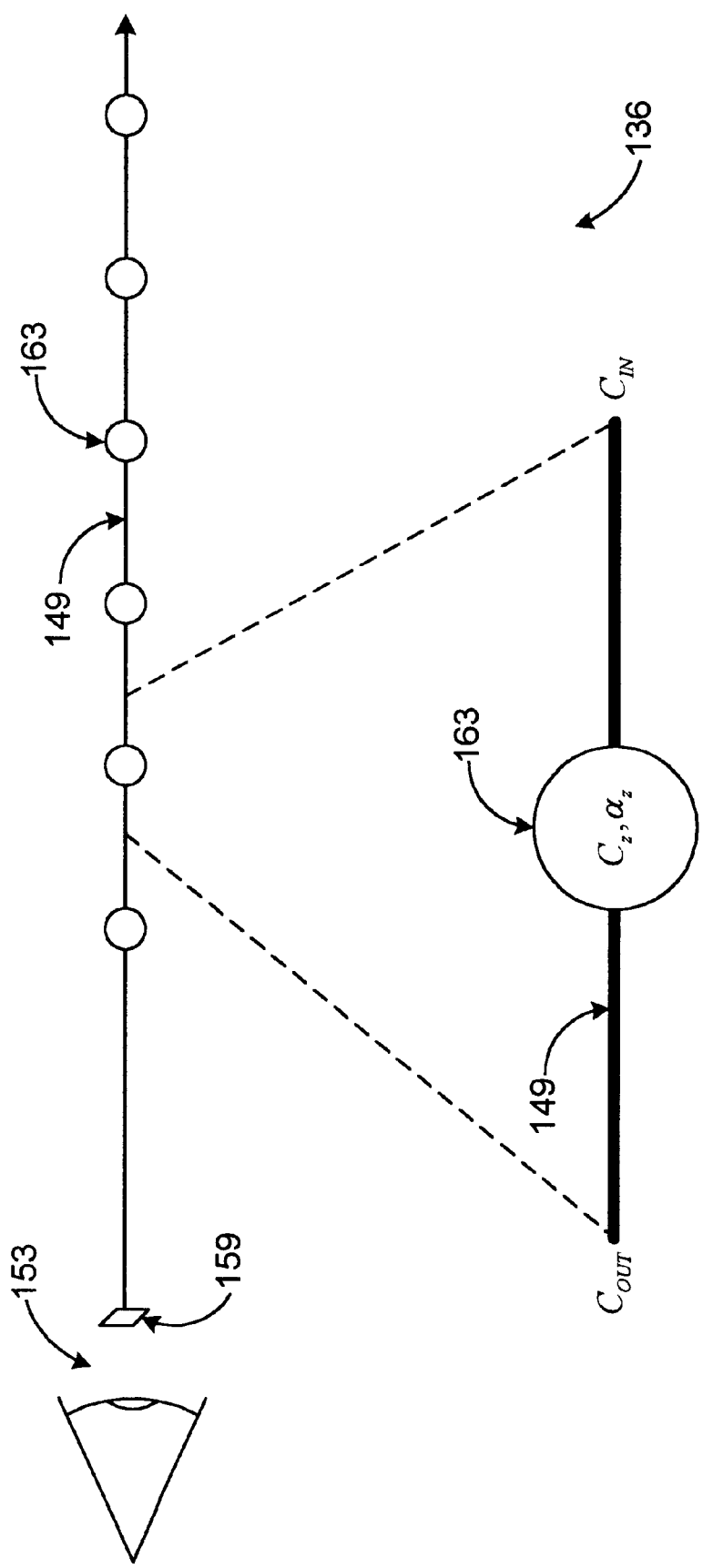

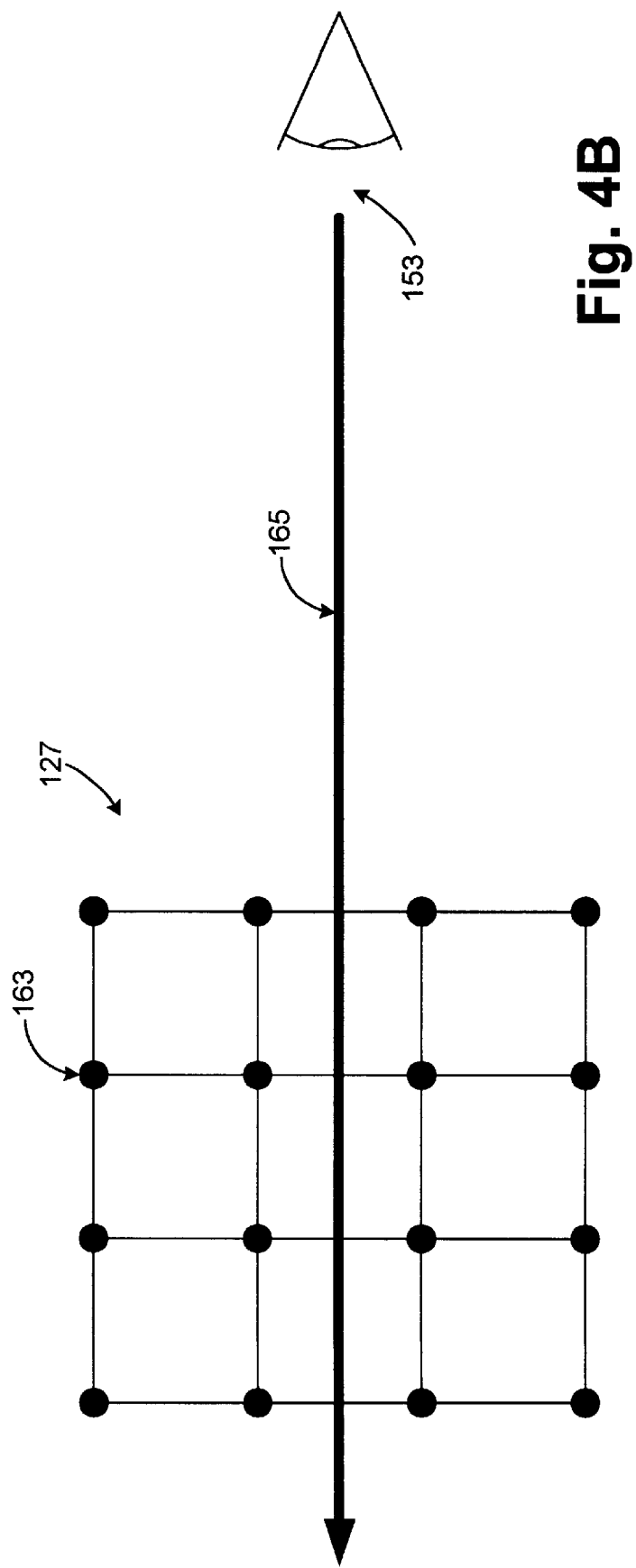

SYSTEM AND METHOD FOR PROVIDING DEPTH PERCEPTION USING SINGLE DIMENSION INTERPOLATION

TECHNICAL FIELD

The present invention is generally related to ultrasonic imaging and, more particularly, is related to a system and method for efficiently providing depth perception in two dimensional renderings of volumetric data using single dimension interpolation.

BACKGROUND OF THE INVENTION

Modern high performance ultrasound imaging systems are currently used for medical applications and other uses. Generally, such systems employ a sonic transducer to emit a sonic pulse through a medium such as the human body which generates echoes. These echoes are received by the transducer or other sensors captured in data that is stored and ultimately used to generate images on a display. Such images or renderings can be shown in real time to see movement within the medium, for example, the beating of a heart in a human body, or the renderings may be frozen in time, taking a snapshot of the medium at a given moment.

Attempts to achieve three dimensional renderings of various media have achieved limited success. In particular, such renderings are achieved in a time consuming, off-line process which is usually manually interactive. This fact limits the usefulness of such technology for use in medical or other related fields. In addition, for non-moving or frozen three dimensional renderings in particular, it is very difficult to appreciate the various features shown in such renderings due to a lack of depth perception. In particular, frozen three dimensional renderings do not have moving components which generally give a clue as to the depth of the component relative to other components as seen by the observer. Additionally, such renderings are characterized by a significant amount of gray speckle which makes it even more difficult to ascertain the features of the renderings obtained, even for those with significant experience viewing such renderings.

SUMMARY OF THE INVENTION

The present invention provides a system and method for generating two dimensional renderings on a display device of acoustic volumetric data that provides depth perception to the user.

Briefly described, in architecture, the system can be implemented as follows. An acoustic data acquisition circuit which includes a sonic transducer and other components generates and stores an acoustic data set from medium such as a human body, etc. The system includes a scan converter that generates a perspective volumetric data set of the medium based upon the acoustic data set, and a single dimensional interpolator that generates at least one interpolated data set from the perspective volumetric data set. The perspective volumetric and interpolated data sets are processed by a compositor that generates two dimensional renderings of the perspective volumetric data set and the interpolated data sets. The system includes a display device which displays the two dimensional renderings in a predetermined fashion.

The present invention can also be viewed as providing a method for generating images using an ultrasound imaging system, comprising the steps of: generating an acoustic data set; generating a perspective volumetric data set of a medium from an acoustic data set; generating at least one interpolated data set from the perspective volumetric data set; and, displaying a two dimensional rendering of the perspective volumetric data set and the at least one interpolated data set on a display in a manner to provide depth perception of the medium.

The present invention provides the ability to produce frozen and unfrozen two dimensional renderings of a medium in order to enhance depth perception and overall perception of the medium.

The present invention has numerous advantages, a few of which are delineated hereafter as merely examples. In particular, the present invention provides a fast and simple system and method to generate at least one second two dimensional rendering of a medium to enhance a user's perception of depth of the medium. Other advantages of the invention include the fact that it is simple in design, user friendly, robust and reliable in operation, efficient in operation, and easily implemented for mass commercial production.

Other features and advantages of the present invention will become apparent to one with skill in the art upon examination of the following drawings and detailed description. It is intended that all such additional features and advantages be included herein within the scope of the present invention.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 3 is a drawing showing the function of the compositor of the imaging system of FIG. 1;

FIG. 4B is a top view of the rectangular volumetric data set of FIG. 4A; and

DETAILED DESCRIPTION OF THE PREFERRED EMBODIMENT

Figure 1:
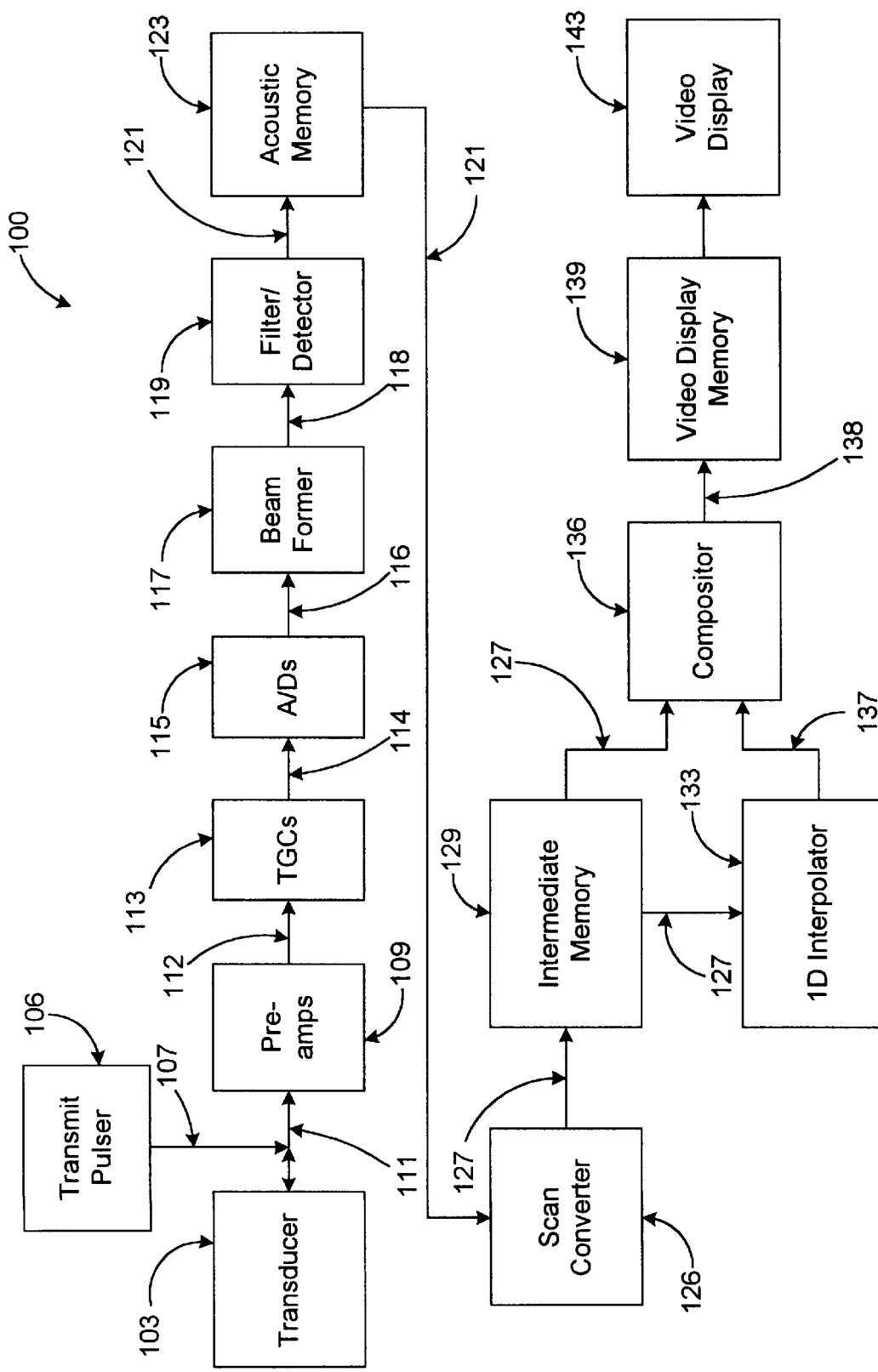
FIG. 1 is a functional block diagram of an imaging system according to an embodiment of the present invention.

Turning to FIG. 1, shown is a block diagram of an ultrasound imaging system 100 according to an embodiment of the present invention. The architecture of the ultrasound imaging system 100 of the present invention is illustrated by way of a functional block diagram in FIG. 1. Note that each block of FIG. 1 defines a logical function that can be implemented in hardware, software, or a combination thereof. For purposes of achieving high speed, it is preferred, at present, that most of the blocks be implemented in hardware, unless specifically noted hereafter.

An ultrasound imaging system 100 further includes an ultrasonic transducer 103 configured to emit and receive ultrasound signals, or acoustic energy, respectively to and from an object under test (e.g., a body or a patient when the ultrasound imaging system 100 is used in the context of a medical application). Many types of transducers 103 are known in the art and are suited for use in connection with the present invention.

In the preferred embodiment, the transducer 103 comprises an array of elements typically made of a piezoelectric material, for example but not limited to, crystal. Each element is voltage biased and supplied with an electrical pulse or other suitable electrical waveform, causing the elements to collectively propagate an ultrasound pressure wave into the object under test. Moreover, in response thereto, one or more echoes are emitted by the object under test and are received by the transducer 103, which transforms the echoes into an electrical signal for further processing.

The array of elements associated with the transducer 103 enable a beam, emanating from the transducer array, to be steered (during transmit and receive modes) through the object by shifting the phase (introducing a time delay) of the electrical pulses/biasing signals supplied to the separate elements. During transmit, an analog waveform is communicated to each transducer element, thereby causing a pulse to be selectively propagated in a particular direction, like a beam, through the object. Note that there are a number of other techniques to steer the beam including linear translation which are known by those skilled in the art and not discussed in detail herein.

During the receive mode, an analog waveform is received at each transducer element at each beam position. Each analog waveform essentially represents a succession of echoes received by the transducer element over a period of time as echoes are received along the single beam through the object. The entire set of analog waveforms represents an acoustic line, and the entire set of acoustic lines represents a single view, or image, of an object and is referred to as a frame.

A transmit pulser 106 is electrically connected to the transducer and generates electrical pulses 107 that are periodically communicated to the array of elements of the transducer 103, causing the transducer elements to emit ultrasound signals into the object under test of the nature described previously. The transmit pulser 106 typically provides separation between the pulse transmissions to enable the transducer 103 to receive echoes from the object during the period therebetween and forwards them onto a set of parallel analog preamplifiers 109.

The plurality of preamplifiers 109 receives a collection (for each separate acoustic line) of analog electrical echo waveforms 111 from the transducer 103 that are generated by echoes emitted from the object under test. More specifically, each preamplifier 109 receives an analog electrical echo waveform from a corresponding transducer element. Moreover, the set of preamplifiers 109 receives a series of waveform sets, one set for each separate acoustic line, in succession over time and processes the waveforms in a pipeline processing manner. The set of preamplifiers 109 is configured to amplify the echo waveforms 111 to provide amplified echo waveforms 112 in order to enable further signal processing, as described hereafter. Because the ultrasound signals received by the transducer 103 are of low power, the set of preamplifiers 109 should be of sufficient quality that excessive noise is not generated in the process.

Because the echo waveforms typically decay in amplitude as they are received from progressively deeper depths in the object under test, the plurality of analog preamplifiers 109 in the system 100 are connected respectively to a parallel plurality of time-gain compensators (TGCs) 113, which are known in the art and which are designed to progressively increase the gain during each acoustic line, thereby reducing the dynamic range requirements on subsequent processing stages. Moreover, the set of TGCs 113 receives a series of waveform sets, one set for each separate acoustic line, in succession over time and processes the waveforms in a pipeline processing manner.

A plurality of parallel analog-to-digital (A/D) converters 115 is connected respectively to the plurality of TGCs 113, as shown in FIG. 1. Each of the A/D converters 115 is configured to convert its respective analog echo waveform 114 into a digital echo waveform 116 comprising a number of discrete location points (hundreds to thousands; corresponds with depth and may be a function of ultrasound transmit frequency) with respective quantized instantaneous signal levels, as is well known in the art. In previous prior art ultrasound imaging systems, this conversion often occurred later in the signal processing steps, but now, many of the logical functions that are performed on the ultrasonic signals can be digital, and hence, the conversion is preferred at an early stage in the signal processing process. Similar to the TGCs 113, the plurality of A/D converters 115 receive a series of waveforms for separate acoustic lines in succession over time and processes the data in a pipeline processing manner.

A beamformer 117 is connected to the A/D converters 115 and is designed to receive the multiple digital echo waveforms 116 (corresponding with each transducer element) from the A/D converters 115 and combine them to form a single acoustic line 118. To accomplish this task, the beamformer 117 delays the separate echo waveforms 116 by different amounts of time and then adds the delayed waveforms together, in order to create a composite digital RF acoustic line 118. The foregoing delay and sum beamforming process is well known in the art. In addition, the beamformer 117 receives a series of data collections for separate acoustic lines in succession over time and processes the data in a pipeline processing manner.

The beam former 117 is coupled to filter/detector 119 which further processes the composite digital RF acoustic line 118 as known in the art and not described in detail herein. Thereafter, the filter/detector 119 outputs acoustic data sets 121 which are stored in an acoustic memory 123 for further processing. Generally the operation of the above described components is known to those skilled in the art and, consequently, they are not described in detail herein. For purposes of the present discussion, the foregoing components including the transducer 103 through the acoustic memory 123 are termed an acoustic data acquisition circuit.

The acoustic memory 123 is coupled to a scan converter 126 which accesses and processes the acoustic data sets 121, generating perspective volumetric data sets 127 which comprises a number of voxels arranged along a number of first perspective viewing rays as will be discussed. To facilitate the discussion herein, the perspective volumetric data sets 127 include rectangular volumetric data sets which have a viewpoint that is located at an infinite distance away, resulting in parallel viewing rays. These concepts will be discussed in later text herein.

The scan converter 126 is in turn coupled to an intermediate memory 129 where the perspective volumetric data sets 127 are stored. The intermediate memory 129 includes two outputs, one of which is coupled to a single dimension (1 D) interpolator 133, and the second of which is coupled to a compositor 136. The 1 D interpolator 133 includes an output which is also coupled to the compositor 136. The 1 D interpolator 133 accesses the perspective volumetric data sets 127 stored in the intermediate memory 129 and generates a predetermined number of corresponding interpolated perspective volumetric data sets 137 (hereafter "interpolated data sets 137"). Each interpolated data set 137 comprises a number of interpolated voxels which are obtained using a respective perspective volumetric data set 127. For each interpolated data set 137, the interpolated voxels are arranged along a number of interpolated perspective viewing rays as will be discussed. The 1 D interpolator may generate any number of interpolated data sets 137 from a single perspective volumetric data set 127. These multiple interpolated data sets 137 are employed to achieve two dimensional (2 D) renderings of the medium in a manner according to the present invention as is detailed in later text.

The compositor 136 receives both the perspective volumetric data sets 127 and the interpolated data sets 137 from the intermediate memory and the 1 D interpolator 133 and generates a two dimensional (2 D) rendering 138 for each. The two dimensional renderings 138 are stored on a video display memory 139 which is coupled to the compositor 136. The video display memory 139 in turn is coupled to a video display 143. The video display 143 depicts the 2 D rendering on a screen which may be a cathode ray tube, a liquid crystal display screen, or other similar display device.

Note that the block diagram of FIG. 1 indicates logic and functions which may be implemented in hardware, software, firmware, or a combination thereof. Due to an extremely large amount of calculation performed in a given amount of time in order to perform real time 2 D renderings on the video display, many of the logic and functions described herein are implemented using dedicated logical circuits to increase the speed of the overall system. In some cases, a fast digital signal processor or other processor circuit which includes a processor and a memory coupled to a data bus to perform selected blocks above in which the logical functions are embodied in software or firmware that is executable by the processor. The particular configuration of processor circuits with software or firmware, dedicated logical circuits, and other hardware used to create the imaging system 100 is left to the one skilled in the art taking into account the speed requirements and other design factors.

In addition, any of the above mentioned functional blocks implemented in software comprising an ordered listing of executable instructions for implementing logical functions, can be embodied in any computer-readable medium for use by or in connection with an instruction execution system, apparatus, or device, such as a computer-based system, processor-containing system, or other system that can fetch the instructions from the instruct execution system, apparatus, or device and execute the instructions. In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (magnetic), a read-only memory (ROM) (magnetic), an erasable programmable read-only memory (EPROM or Flash memory) (magnetic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

Figure 2:
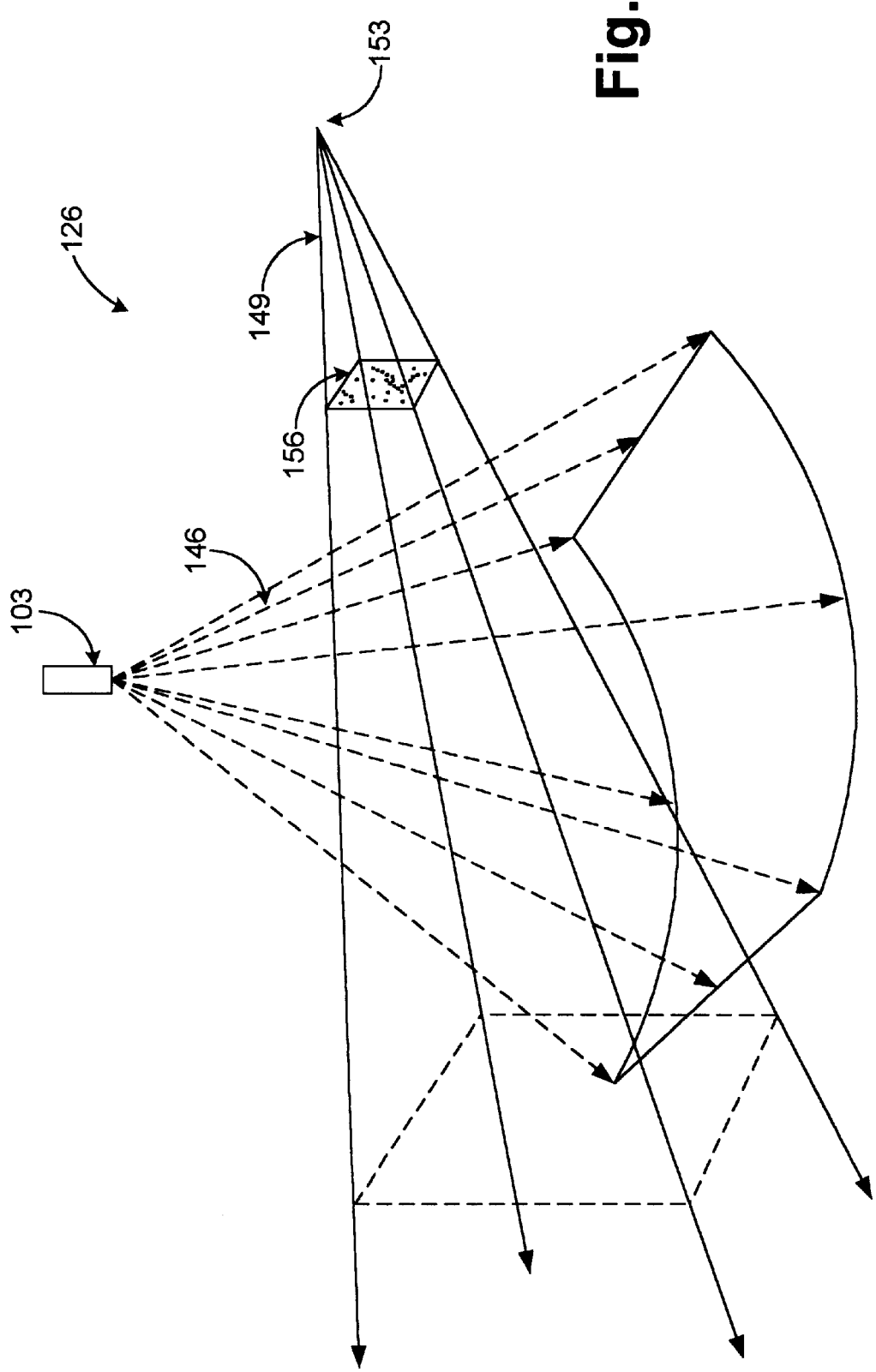
FIG. 2 is a drawing illustrating the function of the scan converter of the imaging system of FIG. 1.

Referring to FIG. 2, shown is an illustration of the functionality of the scan converter 126 (FIG. 1) according to an embodiment of the present invention. The acoustic data sets 121 which are stored in the acoustic memory 123 may be in rectangular or polar coordinates. For example, the transducer 103 may obtain the acoustic data sets 121 along acoustic lines 146 which are directed throughout the volume of the medium (not shown) from the transducer 103 either in a polar or linear translational manner. The coordinates of the acoustic data sets are traced to perspective coordinates along the perspective ray trace lines 149 which extend from a predetermined first viewpoint 153, thereby generating respective perspective volumetric data sets 127. The perspective volumetric data sets 127 are then stored in the intermediate memory 129 (FIG. 1). The perspective volumetric data sets 127 may be used to generate a two-dimensional rendering 156 of the medium. Note that the perspective ray trace lines 149 may be in parallel if a loss of perspective is not important, which results in a rectangular volumetric data set 127. That is to say, that the perspective ray trace lines 149 would be rectangular ray trace lines in which the first viewpoint 153 is assumed to be an infinite distance away from the acoustic data sets 121. As contemplated herein, the volumetric data sets 127 may be either rectangular or perspective in nature. The precise calculations and other functions performed to accomplish the tracing of the acoustic data set coordinates to the perspective coordinates are known by those skilled in the art and not discussed in detail herein.

With reference to FIG. 3, shown is an illustration which depicts the logic of the compositor 136 (FIG. 1) according to an embodiment of the invention. The compositor 136 determines the output of a number of pixels 159 of the video display 143 of the 2 D rendering 138 (FIG. 1) where each pixel 159 extends from a particular perspective ray trace line 149. The acoustic data sets 121 (FIG. 1) are each comprised of several voxels 163 which have been interpolated along the perspective ray trace lines 149 during the scan conversion process discussed with reference to FIG. 2. The compositor 136 performs an integration function progressively with each voxel 163 to determine the color C of the pixel 159. Starting with the voxel 163 at the farthest distance from the first viewpoint 153, the color $C_{OUT}$ is calculated for each voxel 163 based on the opacity $\alpha_Z$ and the color $C_z$ of the particular voxel 63 considered. $C_{OUT}$ is calculated by the equation $C_{OUT}=C_{IN}(1-\alpha_Z)+C_Z\alpha_Z$, where $C_{IN}$ is equal to the color $C_{OUT}$ calculated by a previous voxel 63. The final $C_{OUT}$ is applied to the pixel 159. Note that there are other approaches of compositing to determine the output of the pixels 159 which are known in the art such as maximum intensity projection, minimum intensity projection, and others that may be used in place of the approach discussed above.

Figure 4A:
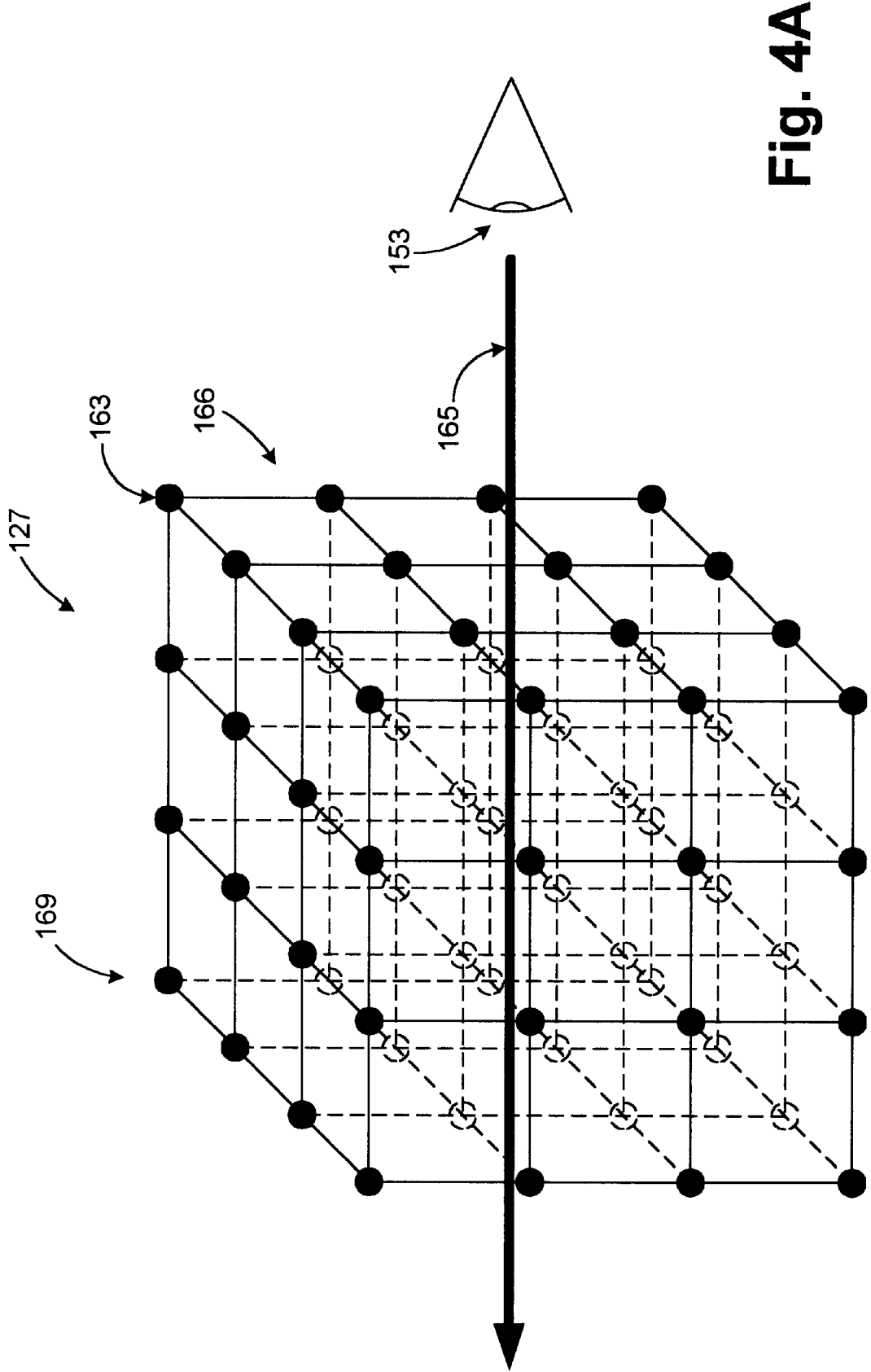
FIG. 4A is a drawing of a rectangular volumetric data set generated by the scan converter of the imaging system of FIG. 1.

Turning then, to FIG. 4A, shown is a rectangular volumetric data set 127 comprising a grid of voxels 163. The voxels 163 have been traced to rectangular ray trace lines 165 which are in parallel. Generally, it is difficult to determined the depth of a 2 D rendering 138 (FIG. 1) that is created by the compositor 136 (FIG. 1) at the first viewpoint 153 of the rectangular volumetric data set 127. Specifically, frontal components 166 may be difficult to distinguish from rear components 169 which results in a 2 D rendering 138 which is difficult to interpret by the end user. FIG. 4B shows a top view of the rectangular volumetric data set 127 of FIG. 4A.

Figure 5:
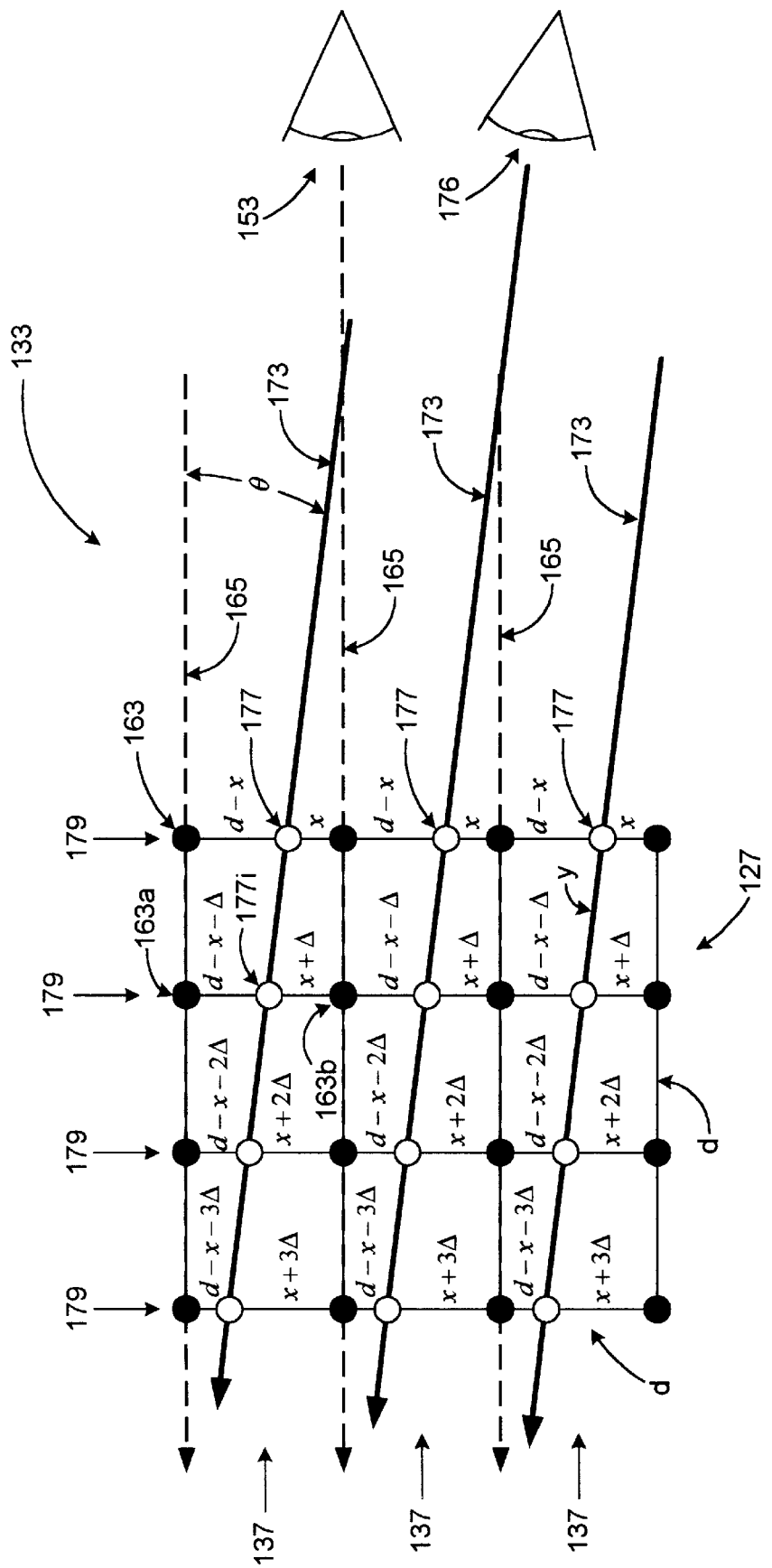
FIG. 5 is a drawing showing the function of the single dimension interpolator of the imaging system of FIG. 1.

With reference to FIG. 5, shown is a second top view of the rectangular volumetric data set 127 and an interpolated data set 137 as determined by the interpolator 133 (FIG. 1). Also depicted are the first viewpoint 153 and rectangular ray trace lines 165 which originate from the direction of the first viewpoint 153, the rectangular ray trace lines 165 being shown in parallel. The voxels 163 which make up the rectangular volumetric data set 127 generated by the scan converter 126 are aligned with the rectangular ray trace lines 165.

The logic of the 1 D interpolator 133 establishes interpolation ray trace lines 173 based upon a second viewpoint 176, the position of which is predetermined. The position of the second viewpoint 176 is determined relative to the first viewpoint 153 by approximating a rotation from the first viewpoint 153 in a single dimension so that the interpolation ray trace lines 173 lie at an angle θ with respect to the rectangular ray trace lines 165. Note that any angle θ may be specified limited by the appearance of distortion of the 2 D rendering at angles generally greater than 15° to 20° or so. The largest angle θ which is chosen and configured in the logic of the 1 D interpolator 133 is application specific depending upon an acceptable degree of distortion in the 2 D renderings 138 (FIG. 1). Note that the interpolation ray trace lines 173 may be determined based upon calculation performed in real time or they can be predetermined based upon a known acoustic data set 121 (FIG. 1) that is generated by the transducer 103 (FIG. 1).

Given the angle and location of the interpolation ray trace lines 173, the interpolator 133 proceeds to generate interpolated voxels 177. The logic of the interpolator 133 determines the location of the interpolated voxels 177 along the interpolation ray trace lines 173 using a progression of equations that are each applied to individual rectangular voxel layers 179 which are comprised of the voxels 163 which lie in planes perpendicular to the rectangular ray trace lines 165. The voxels 163 of the rectangular volumetric data set 127 are arranged in the three dimensional grid with a distance d between any two voxels 163. The locations of the interpolated voxels 177 which are interpolated from the voxels 163 of the first rectangular voxel layer 179 are offset from the positions of the voxels 163 by a distance d−x, given that the x is defined as the distance between the interpolated voxels 177 as they rest on the interpolation ray trace lines 173 and the next adjacent voxel 163 as shown. The positions of the interpolated voxels 177 corresponding to the next voxel layer 179 have been offset by a distance d−x −Δ as shown, where Δ is defined by the equation Δ=y(tan(θ)) and y is the distance between interpolated voxels 177 along the interpolation ray trace lines 173. Further voxel layers 179 are offset by d−x−2Δ, d−x−3Δ, . . . , d−x−NΔ, and so on. As the interpolation ray trace lines 173 cross over the rectangular ray trace lines 165, the progression of equations is continued as the interpolated ray trace lines 173 progress through the rectangular data set 127.

Thereafter, the data values of each of the interpolated voxels 177 are interpolated or determined by a predetermined calculation using the data values of a predetermined number of nearby voxels 163. Specifically, the value of each interpolated voxel 177 is a summation of a fraction of each of the values of nearby voxels 163 where the actual fraction is a function of the distance of the respective voxel 163 from the interpolated voxel 177. For example, the value V of a specific interpolated voxel 177i is calculated by $$V = a\left(\frac{x+\Delta}{d}\right) + b\left(\frac{d-x-\Delta}{d}\right),$$

where a is the value of the voxel 163a and b is the value of the voxel 163b. In this example, only two nearest voxels 163a and 163b are employed to calculate the data value of the interpolated voxel 177i, although the other voxels 163 along the same single dimension of interpolation in all directions may be employed as well. Ultimately, the interpolated data set 137 is applied to the compositor 136 which generates a corresponding 2 D rendering 138 (FIG. 1) as discussed with reference to FIG. 3 that is saved on the video display memory 139 (FIG. 1), and displayed on the video display 143 (FIG. 1).

The present invention provides distinct advantages which includes, but are not limited to the relative simplicity and speed at which an interpolated data set 137 and a corresponding 2 D rendering 138 may be generated based upon a perspective volumetric data set 127 (FIG. 1). In particular, the calculations executed by the logic of the interpolator 133 take less time due to the interpolation in a single dimension and are executable by a relatively simple network of logical components or simple lines of code executed by a processor resulting in faster processing times. As a consequence, multiple interpolated data sets 137 and corresponding 2 D renderings 138 may be obtained quickly in a small amount of time to gain needed depth perception that is missing upon viewing a mere 2 D rendering of the perspective volumetric data set 127 alone. The multiple 2 D renderings 138 of a medium may be employed in a number of ways to bring about an appreciation of the depth of various components and features of the medium. In fact, provided that the processing time is fast enough, the interpolated data sets 137 and multiple 2 D renderings may be viewed in real time to show actual movement.

In one embodiment of the present invention, the multiple 2 D renderings 138 may be employed in a rotational manner. That is to say, that the angle θ for each interpolated data set 137 is set to be a predetermined amount greater than previous interpolated data sets 137. The 2 D renderings 138 that result from the interpolated data sets 137 generated may be shown in progression on the video display 143 resulting in a rotation of the medium on the video display 143. The rotation may be repeated or reversed in direction as often as necessary to ascertain the features of the medium. For example, the slight rotation back and forth may be created, resulting in a wobbling movement or wobbling rotation.

In another embodiment, the 2 D rendering 138 of the perspective volumetric data set 127 and a 2 D rendering 138 of one interpolated data set 137 are generated and alternatively shown on the video display 143. In this case, the transition between 2 D renderings 138 would be rather abrupt rather than a smooth rotation as above. However, such alternating will provide a sense of depth perception to the user and save on processing time.

The rotation or alternating displays above may be used in conjunction when, for example, a real time or unfrozen rendering of the medium is frozen for viewing by means of an input from a keyboard, push button, or other input device. In addition, the wobbling feature may be automatic upon freezing a particular real time 2 D rendering of the medium by some other automated function other than the keyboard, push button, etc. In generating the interpolated data sets, one may also specify the angle θ between the resulting viewpoints as well as the frequency of the wobbling between the 2 D renderings displayed.

In another embodiment, the present invention may provide two 2 D renderings 138 to be used to perform a stereoscopic rendering. In particular, the logic of the interpolator 133 may be configured to generate interpolated data sets 137 and 2 D renderings 138 therefrom which are then be applied to a stereoscopic viewing device. Such devices may include a binocular vision device which exposes each eye of the user to one of the 2 D renderings 138 or the use of two screens in a similar manner. Also, one of the 2 D renderings 138 may be a red 2 D rendering and one a green 2 D rendering which are viewed with special 3 D glasses which allow one eye to view the red 2 D rendering and one eye to view the green 2 D rendering as known in the art.

Many variations and modifications may be made to the above-described embodiment(s) of the invention, which are intended to be non-limiting examples, without departing substantially from the spirit and principles of the invention. All such modifications and variations are intended to be included herein within the scope of the present invention.

What is claimed is:

1. A ultrasound imaging system, comprising:
   an acoustic data acquisition circuit configured to generate and store an acoustic data set;
   a scan converter configured to generate a perspective volumetric data set of a medium based upon the acoustic data set;
   a single dimensional interpolator configured to generate at least one interpolated perspective data set from the perspective volumetric data set;
   a compositor configured to generate a two dimensional rendering of the perspective volumetric data set and at least one two dimensional rendering of the at least one interpolated perspective data set; and
   a display device configured to display the two dimensional renderings of the perspective volumetric data set and the at least one interpolated perspective data set in a manner to provide depth perception of the medium.

2. The system of claim 1, wherein the display device is further configured to progressively display the two dimensional renderings of the perspective volumetric data set and the at least one interpolated perspective data set to approximate a rotation of the medium on the display.

3. The system of claim 1, wherein the display device is further configured to alternate between the display of the two dimensional rendering of the perspective volumetric data set and the interpolated perspective data set.

4. The system of claim 1, wherein the display device further comprises a stereoscopic display device configured to generate a stereoscopic rendering of the medium using the two dimensional renderings of the perspective volumetric data set and the at least one interpolated perspective data set.

5. The system of claim 1, wherein the single dimensional interpolator is further configured to determine an angle between a first viewpoint corresponding to the perspective volumetric data set and at least one second viewpoint corresponding to the at least one interpolated perspective data set.

6. An ultrasound imaging system, comprising:
   acquisition means for acquiring an acoustic data set;
   first means for generating a perspective volumetric data set of a medium from an acoustic data set;
   second means for generating at least one interpolated perspective data set from the perspective volumetric data set, the interpolated perspective data set being interpolated in a single dimension; and
   display means for displaying a two dimensional rendering of the perspective volumetric data set and the at least one interpolated perspective data set on a display in a manner to provide depth perception of the medium.

7. The system of claim 6, wherein the display means further comprises means for progressively displaying the perspective volumetric data set and the at least one interpolated perspective data set to approximate a rotation of the medium on the display.

8. The system of claim 6, wherein the display means further comprises means for alternating between the two dimensional renderings of the perspective volumetric data set and the interpolated perspective data set.

9. The system of claim 6, wherein the display means further comprises means for generating a stereoscopic rendering of the medium using the two dimensional renderings of the perspective volumetric data set and the at least one interpolated perspective data set.

10. The system of claim 6, wherein the second means further comprises means for determining an angle between a first viewpoint corresponding to the perspective volumetric data set and at least one second viewpoint corresponding to the at least one interpolated perspective data set.

11. Method for generating images using an ultrasound imaging system, comprising the steps of:
   generating an acoustic data set;
   generating a perspective volumetric data set of a medium from the acoustic data set;
   generating at least one interpolated perspective data set from the perspective volumetric data set, the interpolated perspective data set being interpolated in a single dimension; and
   displaying a two dimensional rendering of the perspective volumetric data set and the at least one interpolated perspective data set on a display in a manner to provide depth perception of the medium.

12. The method of claim 11, wherein the displaying step further comprises the step of progressively displaying the perspective volumetric data set and the at least one interpolated perspective data set to approximate a rotation of the medium on the display.

13. The method of claim 11, wherein the displaying step further comprises the step of alternating between the two dimensional renderings of the perspective volumetric data set and the interpolated perspective data set.

14. The method of claim 11, wherein the displaying step further comprises the step of generating a stereoscopic rendering of the medium using the two dimensional renderings of the perspective volumetric data set and the at least one interpolated perspective data set.

15. The method of claim 11, further comprising the step of determining an angle between a first viewpoint corresponding to the perspective volumetric data set and at least one second viewpoint corresponding to the at least one at least one interpolated perspective data set.

* * * * *